United States Patent
Lee et al.

(10) Patent No.: US 12,398,376 B2
(45) Date of Patent: Aug. 26, 2025

(54) COMPOSITION COMPRISING NC886 FOR IMPROVING ONCOLYTIC VIRUS ACTIVITY OR PRODUCTION

(71) Applicant: NATIONAL CANCER CENTER, Goyang-si (KR)

(72) Inventors: Yongsun Lee, Goyang-si (KR); Inhoo Kim, Goyang-si (KR); Seungpil Shin, Goyang-si (KR); Sangjin Lee, Paju-si (KR); Yeonsu Lee, Gimpo-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 792 days.

(21) Appl. No.: 17/311,046

(22) PCT Filed: Dec. 6, 2019

(86) PCT No.: PCT/KR2019/017214
§ 371 (c)(1),
(2) Date: Jun. 4, 2021

(87) PCT Pub. No.: WO2020/117003
PCT Pub. Date: Jun. 11, 2020

(65) Prior Publication Data
US 2022/0025338 A1     Jan. 27, 2022

(30) Foreign Application Priority Data
Dec. 6, 2018   (KR) .......................... 10-2018-156446

(51) Int. Cl.
*C12N 7/00*      (2006.01)
*A61K 35/761*    (2015.01)
*A61K 45/06*     (2006.01)

(52) U.S. Cl.
CPC .............. *C12N 7/00* (2013.01); *A61K 35/761* (2013.01); *A61K 45/06* (2013.01); *C12N 2710/10032* (2013.01); *C12N 2799/022* (2013.01)

(58) Field of Classification Search
CPC ............ C12N 7/00; C12N 2710/10032; A61K 35/761
See application file for complete search history.

(56) References Cited

FOREIGN PATENT DOCUMENTS

| KR | 10-2011-0046321 A | 5/2011 | |
|---|---|---|---|
| KR | 10-2012-0131864 A | 12/2012 | |
| KR | 10-2018-0015587 A | 2/2018 | |
| WO | WO-2018001666 A1 * | 1/2018 | ........... A61K 31/712 |

OTHER PUBLICATIONS

Lee YS. A Novel Type of Non-coding RNA, nc886, Implicated in Tumor Sensing and Suppression. Genomics Inform. Jun. 2015;13(2):26-30. (Year: 2015).*
Lee K, Kunkeaw N, Jeon SH, Lee I, Johnson BH, Kang GY, Bang JY, Park HS, Leelayuwat C, Lee YS. Precursor miR-886, a novel noncoding RNA repressed in cancer, associates with PKR and modulates its activity. RNA. Jun. 2011;17(6):1076-89. (Year: 2011).*
Li F, Chen Y, Zhang Z, Ouyang J, Wang Y, Yan R, Huang S, Gao GF, Guo G, Chen JL. Robust expression of vault RNAs induced by influenza A virus plays a critical role in suppression of PKR-mediated innate immunity. Nucleic Acids Res. Dec. 2, 2015;43(21):10321-37. (Year: 2015).*
Masemann D, Kother K, Kuhlencord M, Varga G, Roth J, Lichty BD, Rapp UR, Wixler V, Ludwig S. Oncolytic influenza virus infection restores immunocompetence of lung tumor-associated alveolar macrophages. Oncoimmunology. Feb. 12, 2018;7(5):e1423171. (Year: 2018).*
Matveeva OV, Kochneva GV, Netesov SV, Onikienko SB, Chumakov PM. Mechanisms of Oncolysis by Paramyxovirus Sendai. Acta Naturae. Apr.-Jun. 2015;7(2):6-16. (Year: 2015).*
N Kunkeaw, et al., "Cell death/proliferation roles for nc886, a non-coding RNA, in the protein kinase R pathway in cholangiocarcinoma", Oncogene, 2013, pp. 3722-3731, vol. 32.
Yong Sun Lee, "A Novel Type of Non-coding RNA, nc886, Implicated in Tumor Sensing and Suppression", Genomics & Informatics, 2015, pp. 26-30, vol. 13, No. 2.
Fang Li, et al., "Robust expression of vault RNAs induced by influenza A virus plays a critical role in suppression of PKR-mediated innate immunity", Nucleic Acids Research, 2015, pp. 10321-10337, vol. 43, No. 21.
International Search Report for PCT/KR2019/017214 dated Mar. 24, 2020 (PCT/ISA/210).

* cited by examiner

*Primary Examiner* — Nicole Kinsey White
*Assistant Examiner* — Ruixue Wang
(74) *Attorney, Agent, or Firm* — Sughrue Mion, PLLC

(57) ABSTRACT

The present invention relates to a composition for enhancing oncolytic virus activity which comprises nc886, and a composition for enhancing virus production which comprises the same.

1 Claim, 18 Drawing Sheets
Specification includes a Sequence Listing.

[FIG. 1A]
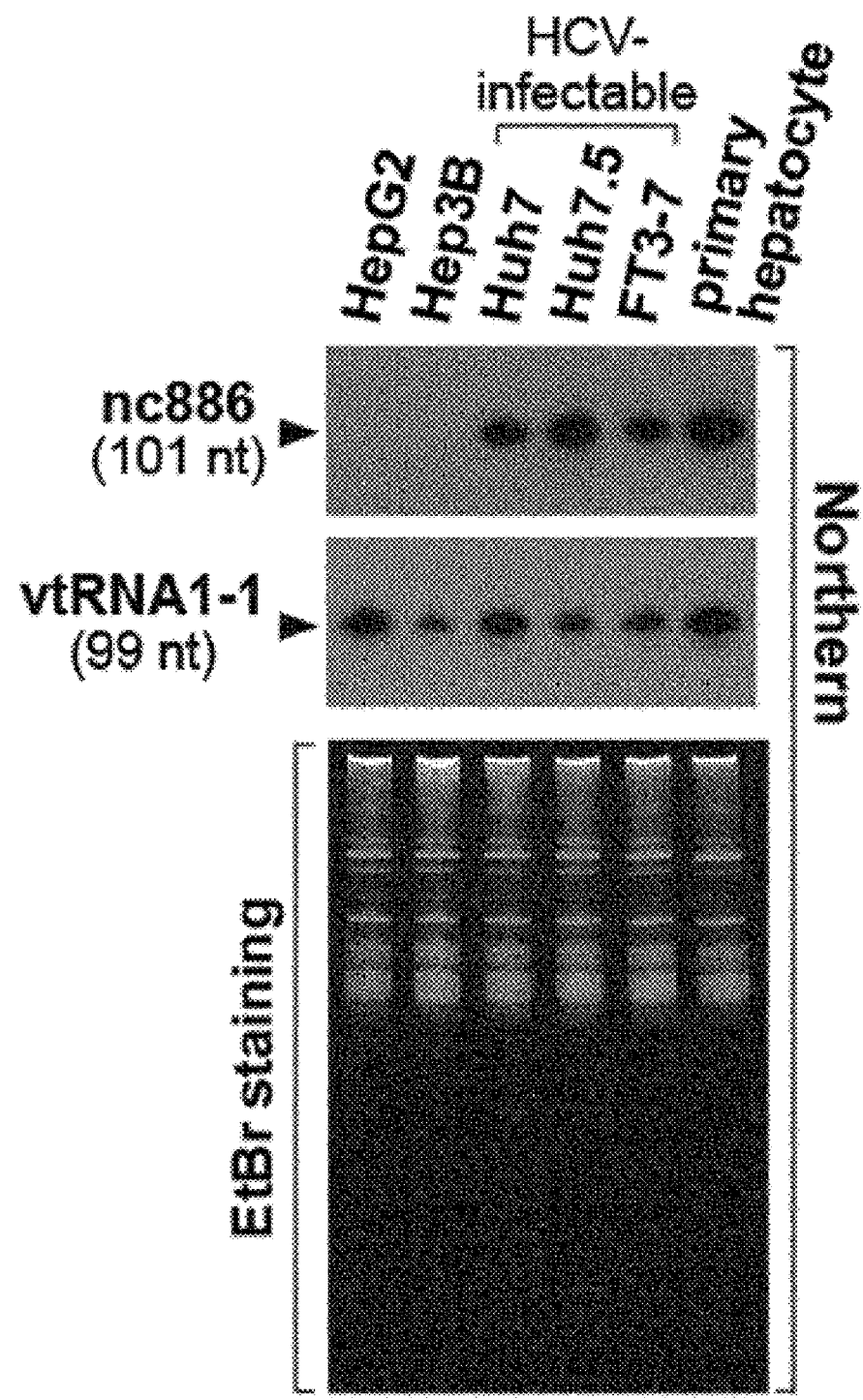

[FIG. 1B]
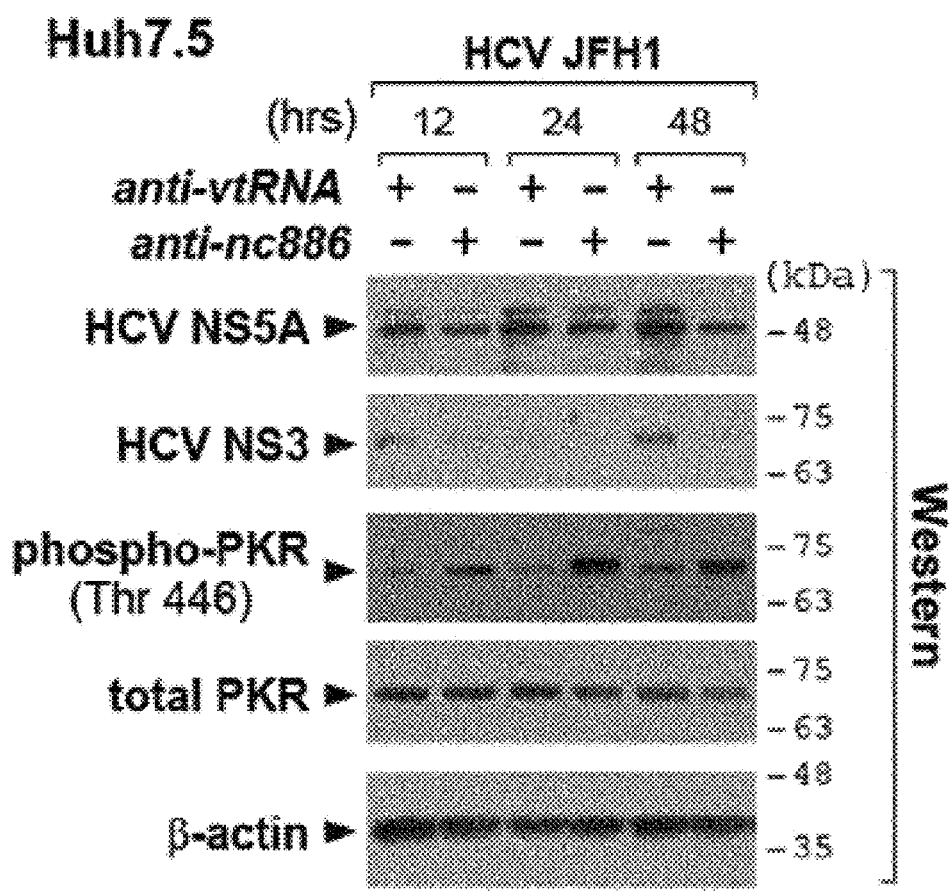

[FIG. 1C]
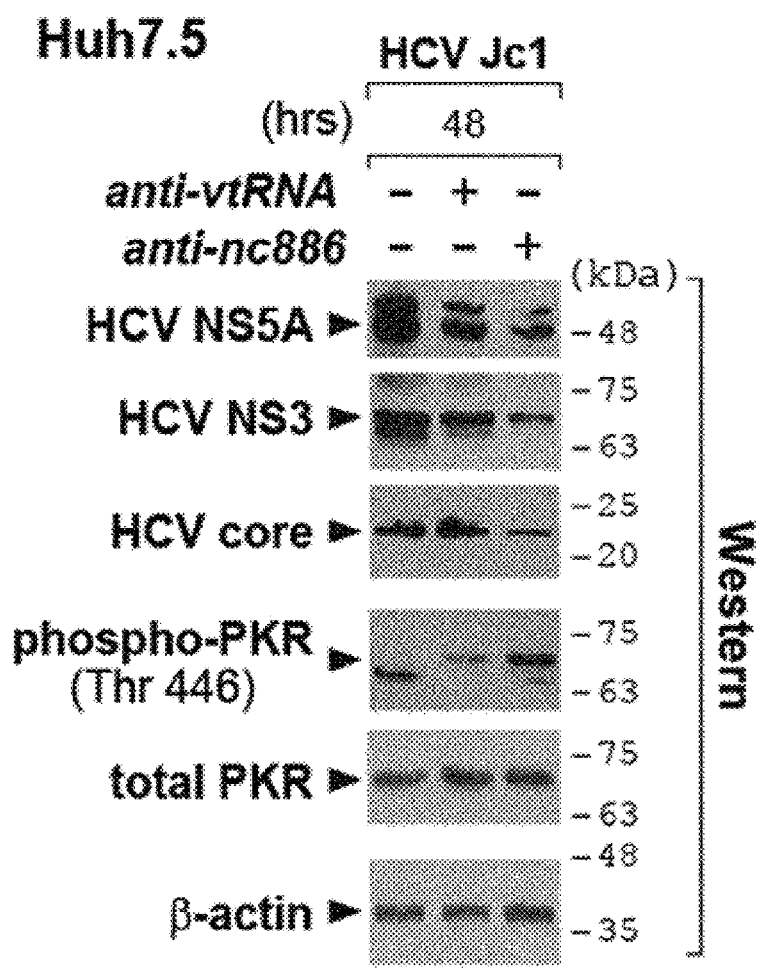

[FIG. 1D]
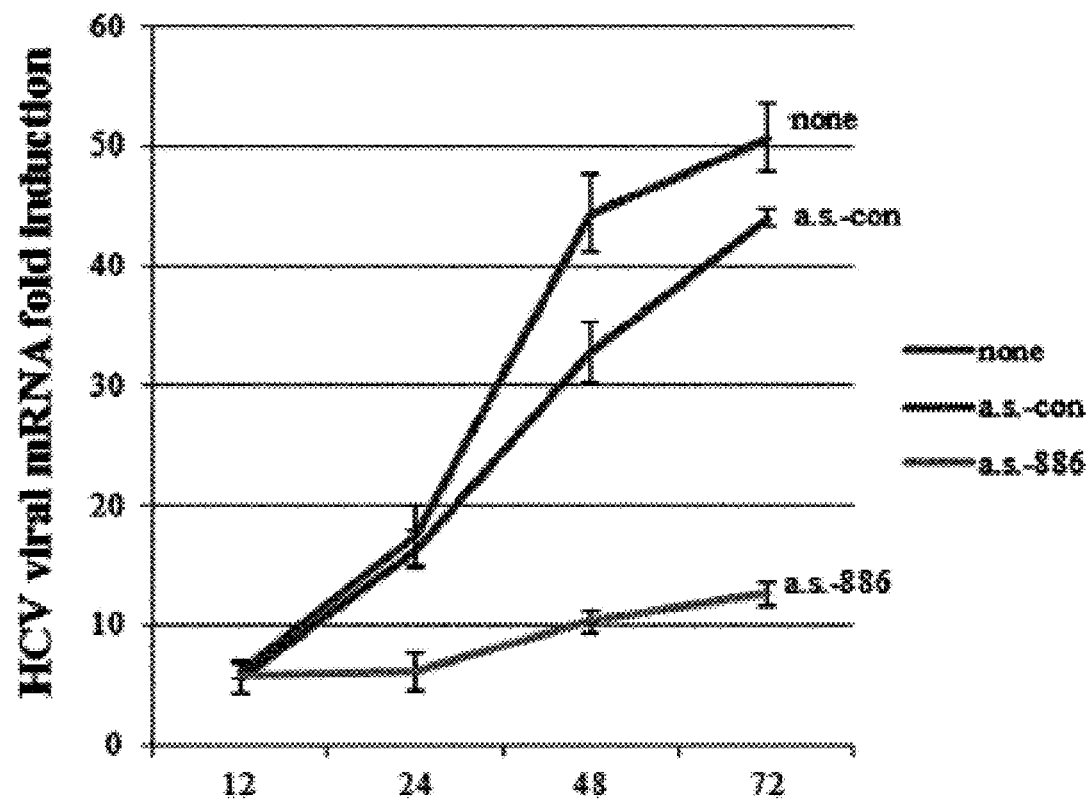

[FIG. 1E]
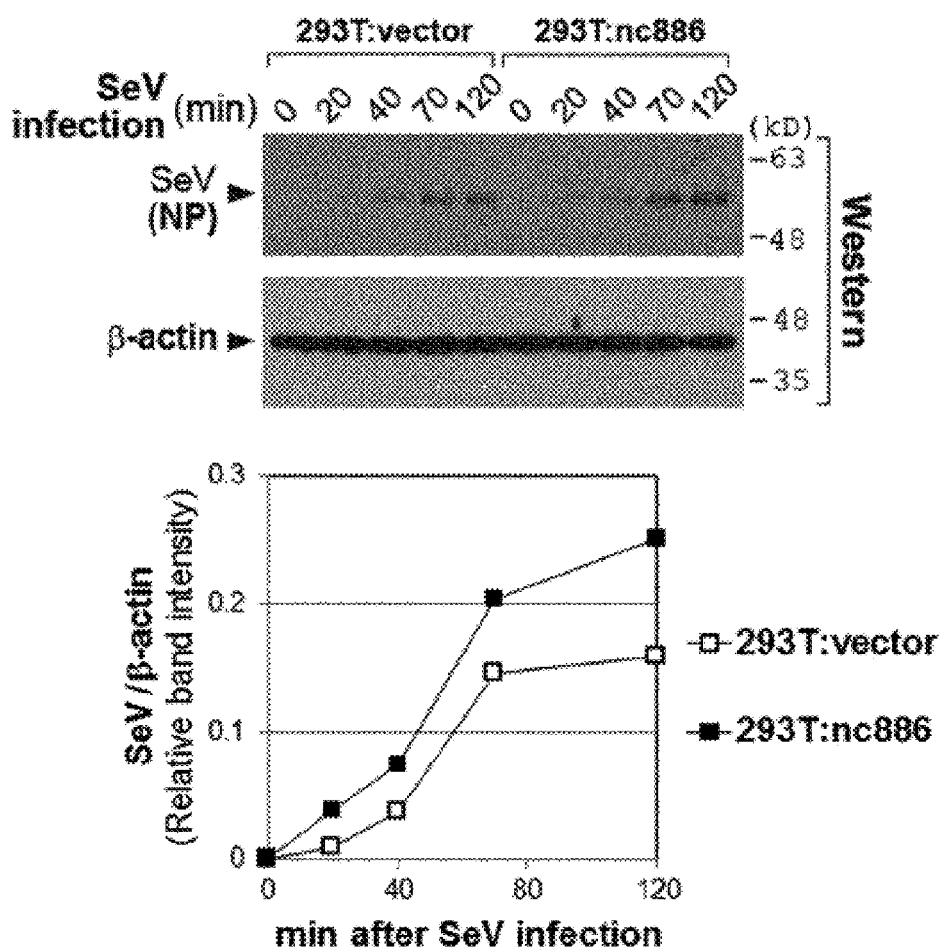

[FIG. 1F]
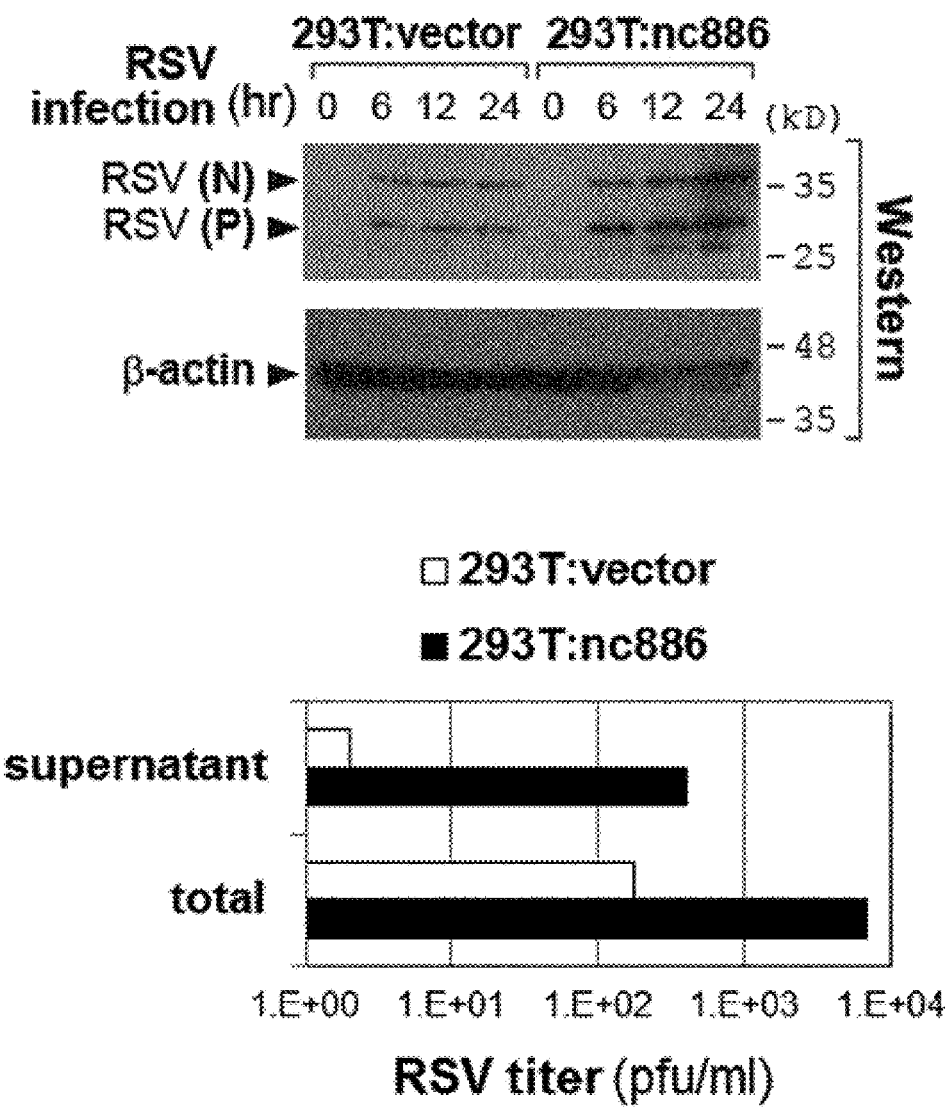

[FIG. 1G]
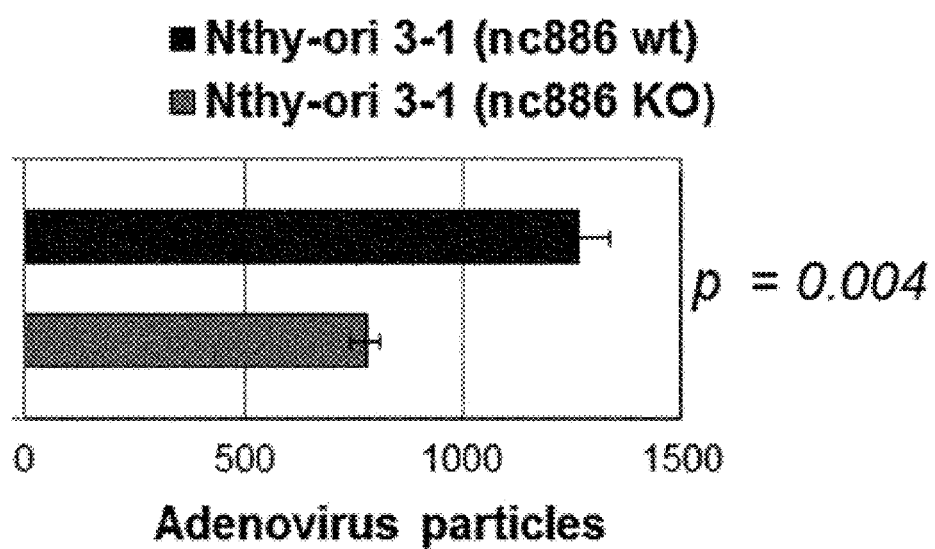

[FIG. 2A]
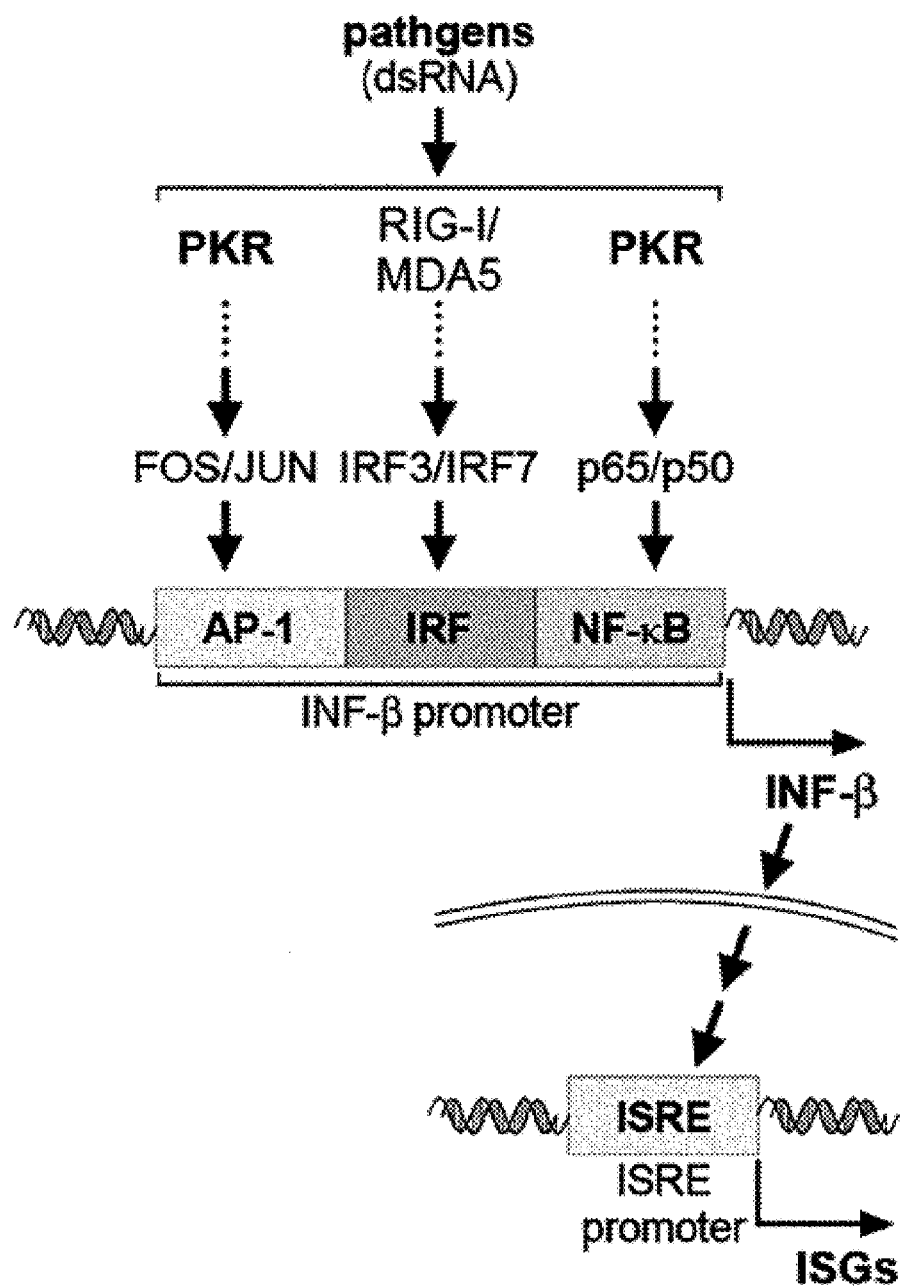

[FIG. 2B]
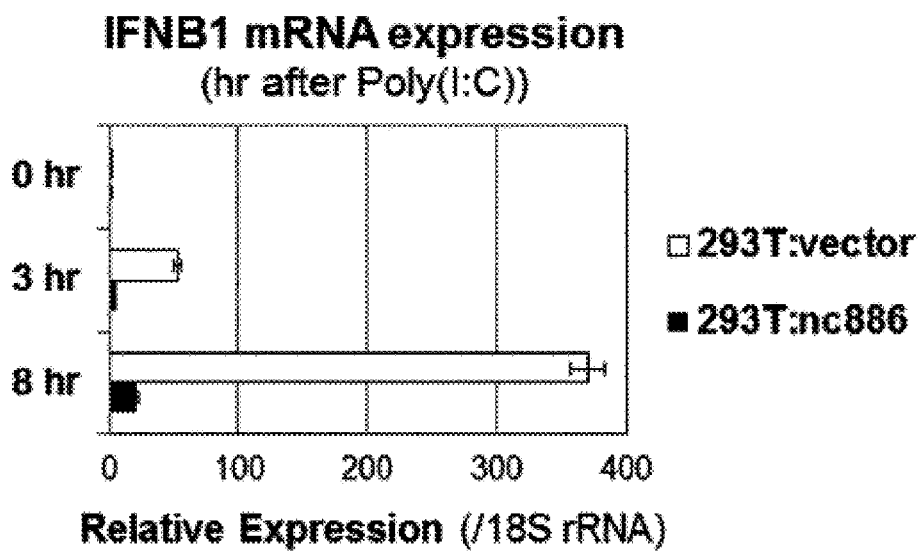
[FIG. 2C]
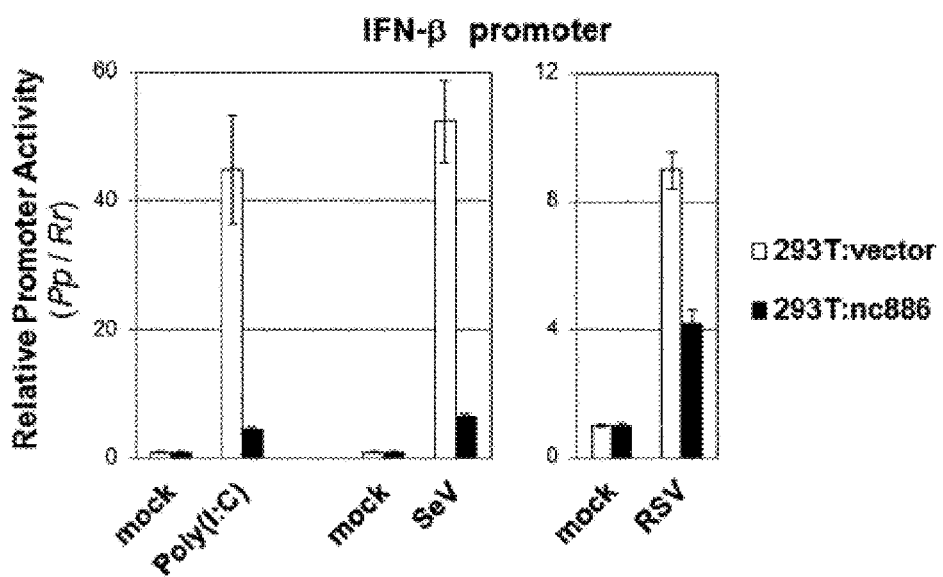

[FIG. 2D]
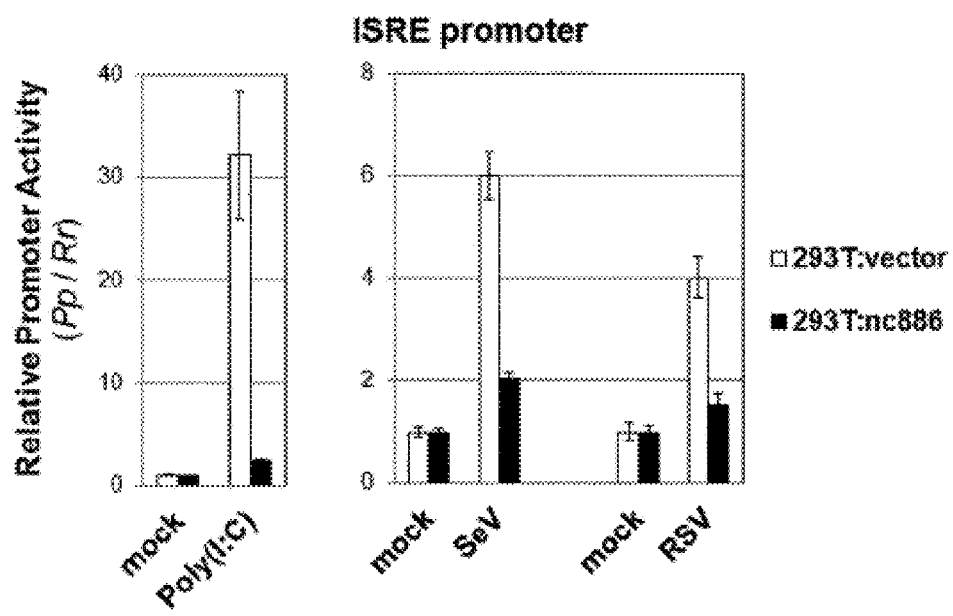

[FIG. 2E]
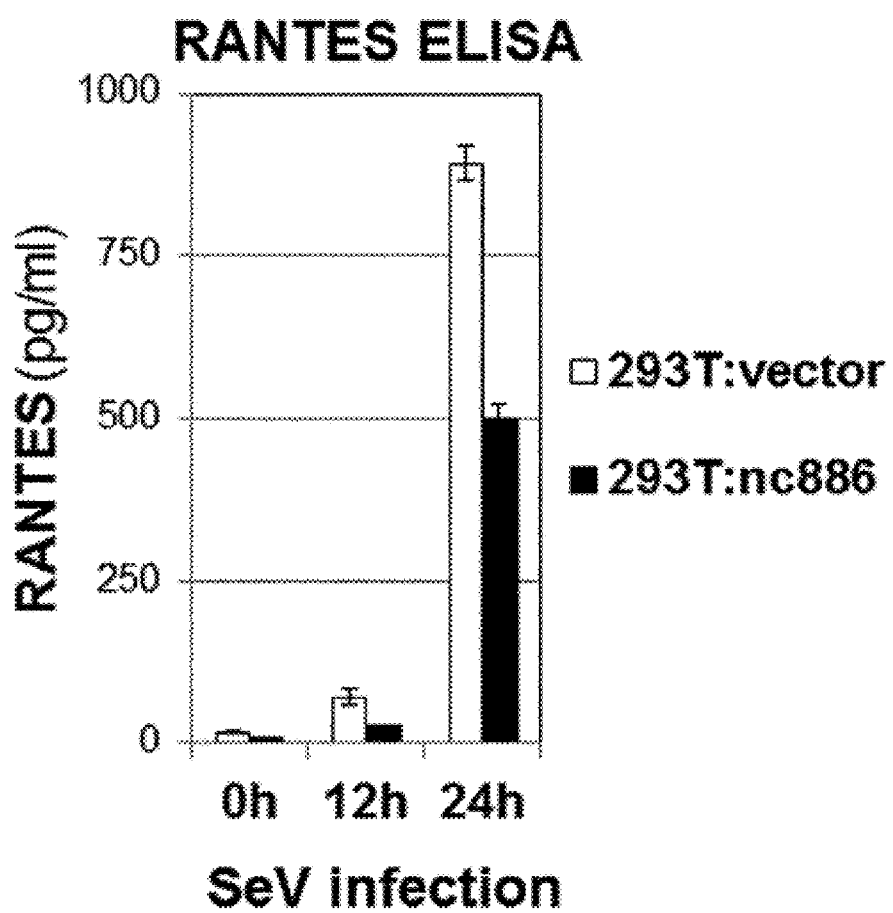

[FIG. 3A]
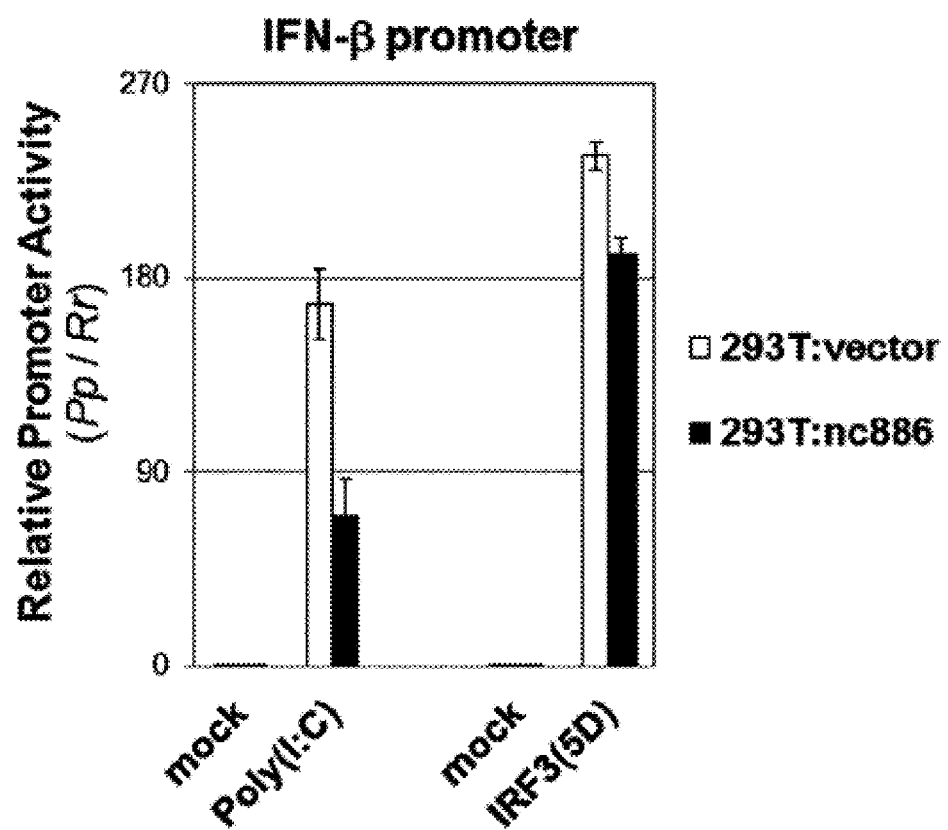

[FIG. 3B]
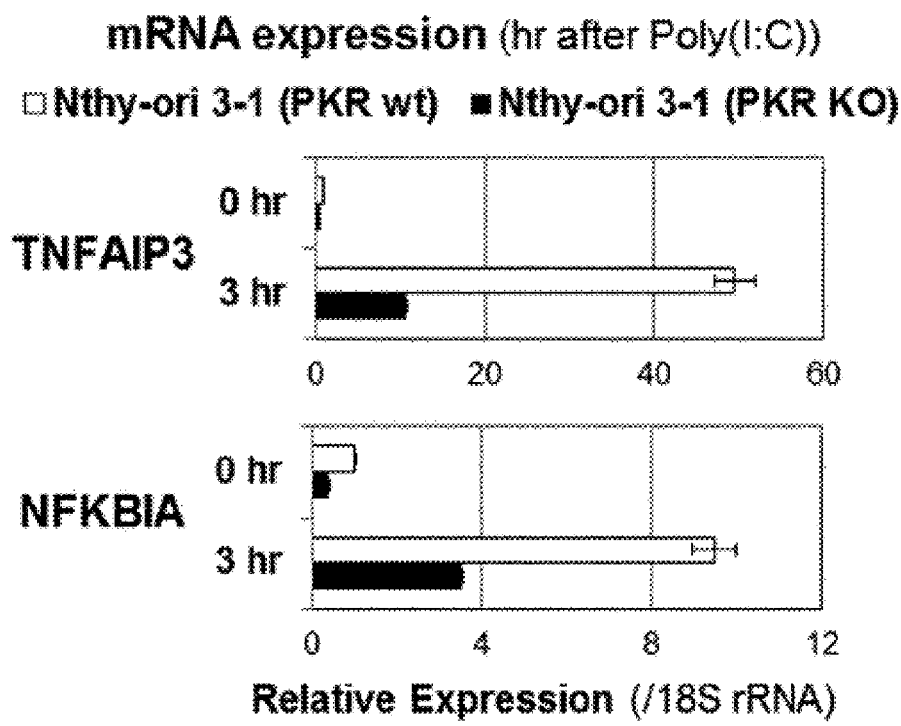

[FIG. 3C]
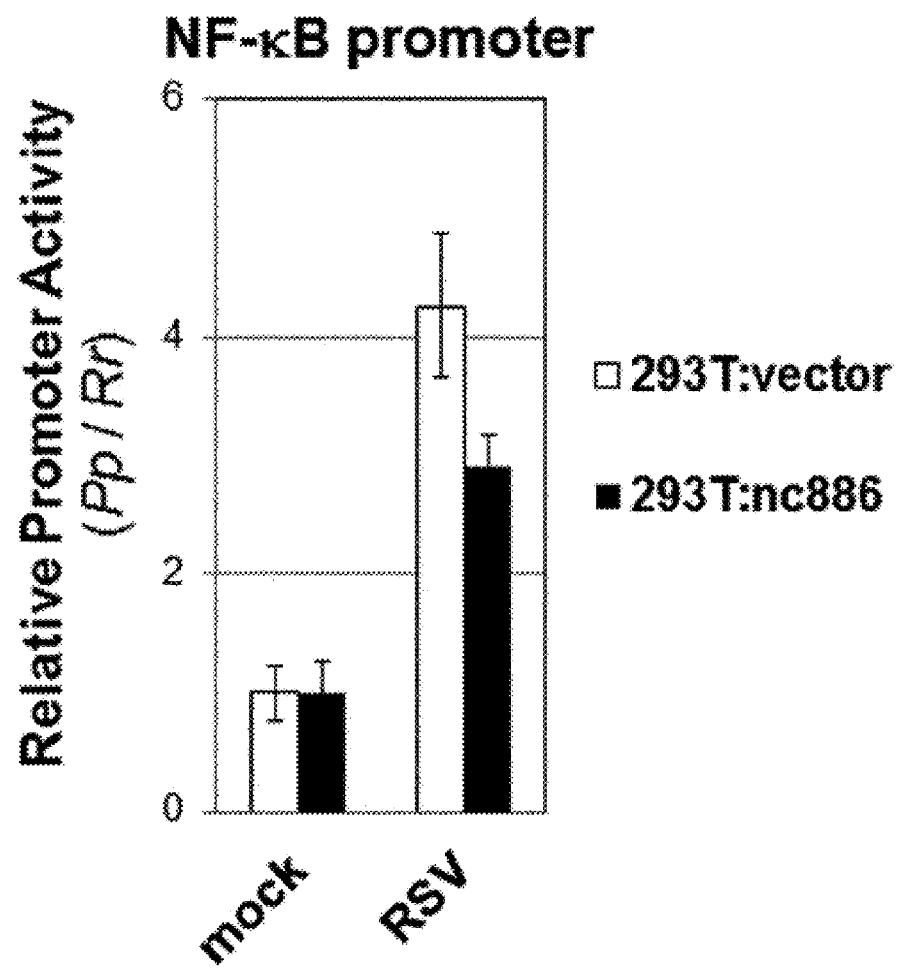

[FIG. 3D]
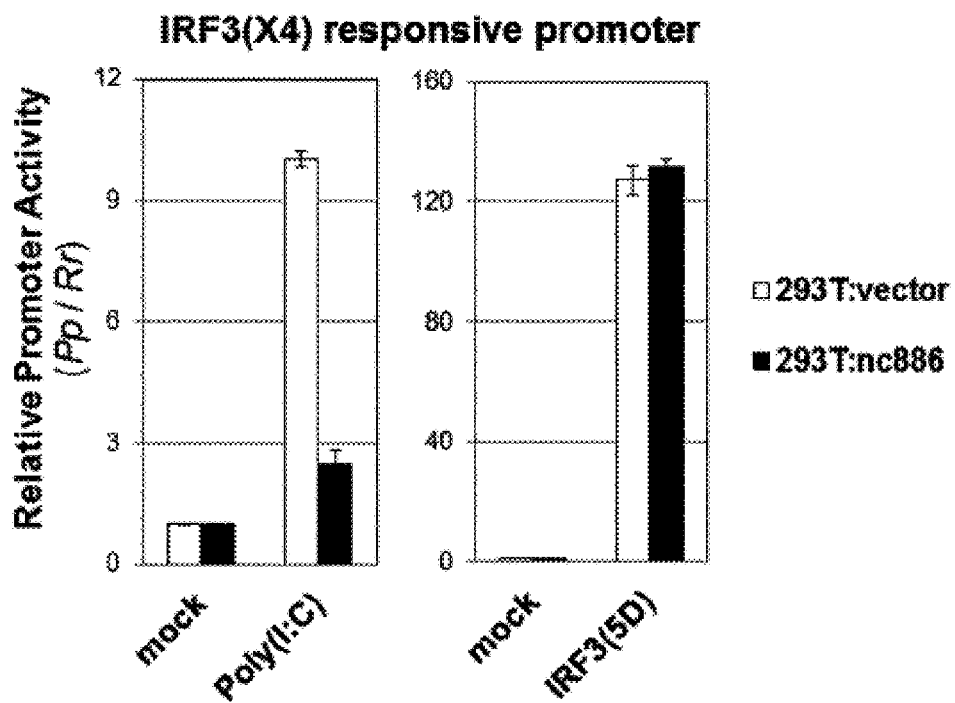
[FIG. 3E]
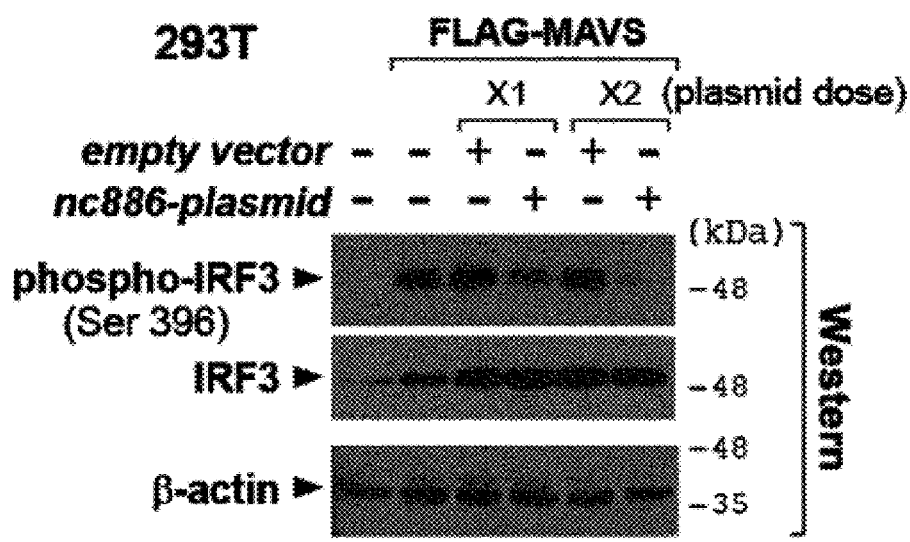

[FIG. 3F]
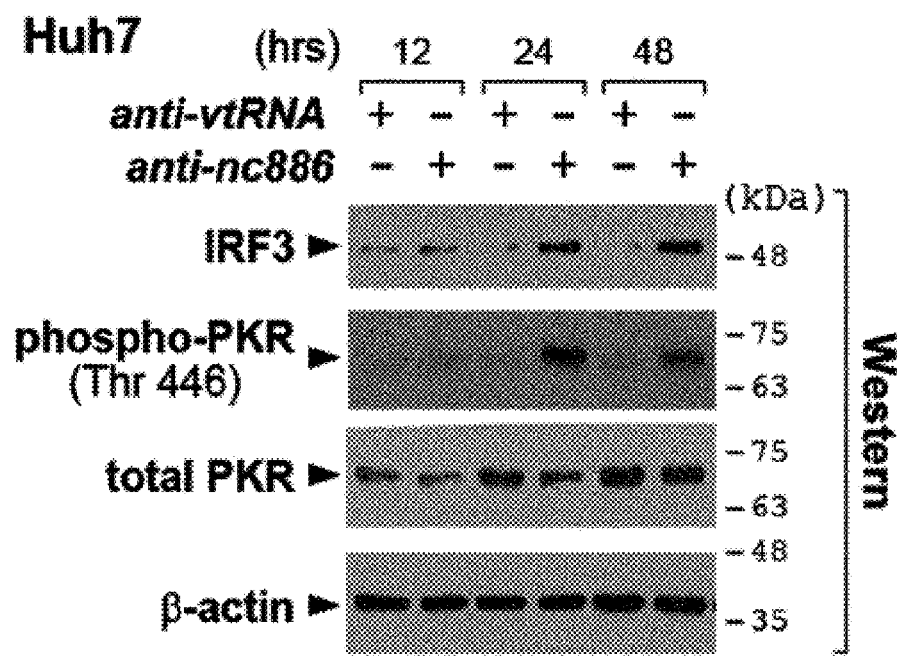

[FIG. 4]
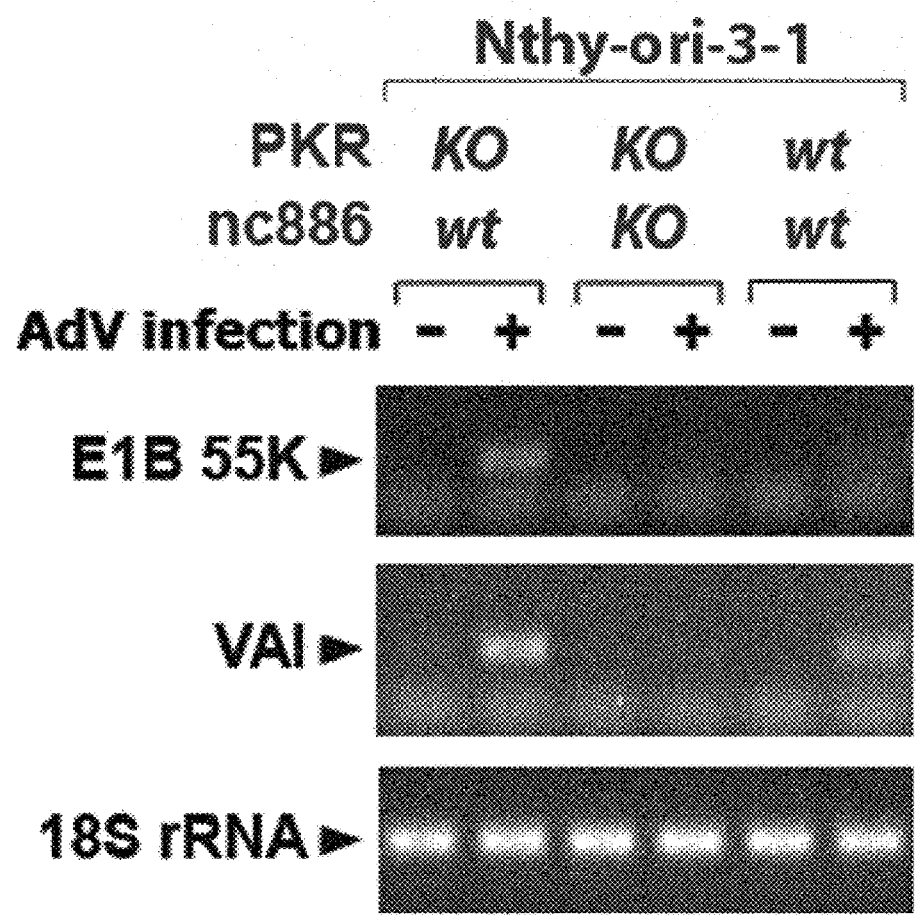

[FIG. 5]
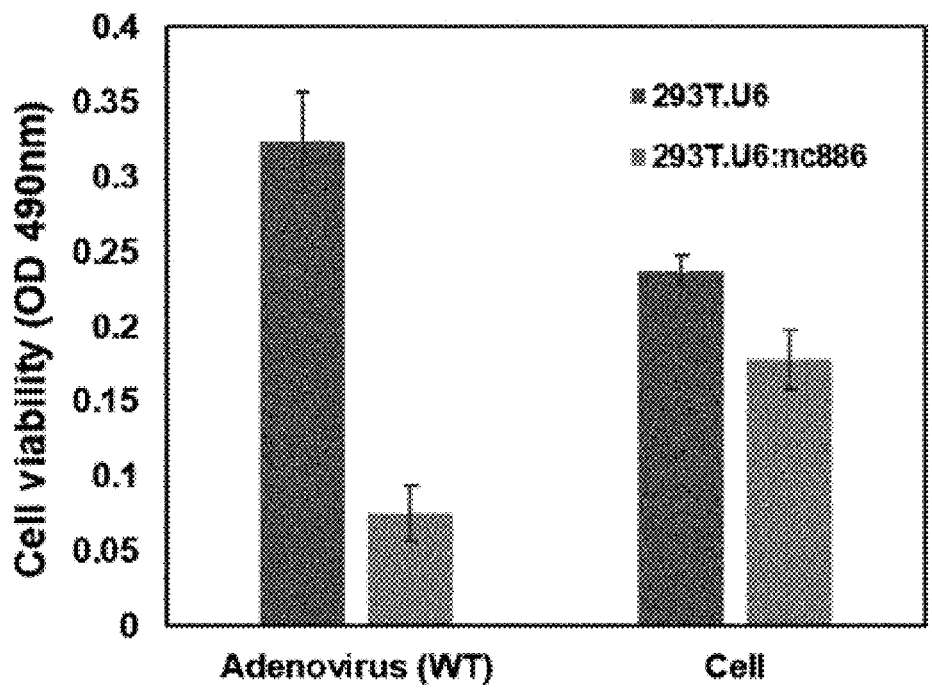

COMPOSITION COMPRISING NC886 FOR IMPROVING ONCOLYTIC VIRUS ACTIVITY OR PRODUCTION

CROSS REFERENCE TO RELATED APPLICATIONS

This application is a National Stage of International Application No. PCT/KR2019/017214 filed Dec. 6, 2019, claiming priority based on Korean Patent Application No. 10-2018-0156446 filed Dec. 6, 2018, the entire disclosures of which are incorporated herein by reference.

TECHNICAL FIELD

The present invention relates to a composition for enhancing oncolytic virus activity which comprises nc886 and a composition for enhancing virus production which comprises the same.

BACKGROUND ART

An oncolytic virus is obtained by manipulating the gene of a live virus and has the following features: The oncolytic virus does not work in normal cells; and proliferates specifically in cancer cells and destroys the cancer cells. In addition to directly attacking cancer cells, the oncolytic virus has a function (immune stimulation) of stimulating the human adaptive immune response as well as a function of inhibiting angiogenesis by specifically infecting and destroying tumor vascular endothelial cells. In 1904, the research team led by G. Dock identified and reported that rabies virus exhibited anticancer activity in cervical cancer patients. Since then, anticancer research has been conducted and reported on viruses such as avian virus and cold virus. Starting with the melanoma therapeutic agent, IMLYGIC® (talimogene laherparepvec), which was developed by Amgen USA, Inc. and first approved for marketing by the U.S. Food and Drug Administration (FDA) in October 2015, many research and clinical trials for oncolytic viruses are attracting attention. However, it is difficult to mass-produce the oncolytic virus, and the oncolytic virus has a problem with insufficient activity in clinical application.

In addition, the oncolytic virus has a problem that in a case where the virus actually enters cells, no treatment occurs due to its low infection rate. Therefore, the oncolytic virus has limited clinical effects, and thus an attempt is currently made for combination therapy with an existing immune checkpoint inhibitor.

Hepatitis C virus (HCV) is a pathogen that is thought to have infected 180 million or more people worldwide, and is known to cause diseases such as liver fibrosis, cirrhosis, and liver cancer if not treated effectively. HCV virus has six genotypes and is evenly distributed around the world, in which the genotypes are distributed differently depending on regions and races. For pathogenic HCV infection, the number of infected people is higher in the order of genotypes 1, 2, and 3. HCV genotype 1 is widely distributed in Europe and North America, and is the most difficult to treat; and HCV genotypes 2 and 3 are prevalent in Far East Asia. In particular, patients with HCV genotype 1, which is difficult to treat, account for the majority of HCV-infected people. Although 1% to 2% of the world's population is infected with this virus, it is very difficult to diagnose because the virus exists in vivo at a very low titer, and there is no effective treatment or vaccine for the HCV virus. Currently, there is a method of simultaneously administering α-interferon and ribavirin which inhibit proliferation of HCV and thus show some effects on diseases caused by HCV. However, it is reported that this method has varying effects on different virus strains; and it is known that this method has a lasting effect in only 40% of HCV-infected patients and causes many adverse effects. Many studies are conducted to solve the above-mentioned problem. For example, Korean Laid-open Patent Publication No. 2012-0131864 discloses a composition for RNA interference, which releases siRNA in a target molecule-specific manner, and a composition for treating HCV related diseases using the same, and Korean Laid-open Patent Publication No. 2011-0046321 discloses a pharmaceutical composition comprising an indole compound. However, due to insufficient therapeutic efficacy of existing viral therapeutic agents, there has been a continuous demand for more effective viral therapeutic agents.

Technical Problem

While studying the recently discovered non-coding RNA, nc886, the present inventors have found that nc886 can promote virus replication to help virus production, and provide a pro-viral environment to enhance virus activity. The present inventors have found that knock-down of nc886 results in a significant decrease in viral mRNA and protein. As such, the present inventors have found that use of an nc886 antagonist has prophylactic and therapeutic effects against viruses. Accordingly, the present invention provides a composition for enhancing oncolytic virus activity which comprises nc886, a composition for enhancing virus production which comprises the same, a method for producing viruses, and a composition for treating viruses which comprises an nc886 antagonist.

In the present invention, virus proliferation is inhibited by administering an nc886 antagonist at an initial stage of viral infection. Rather conversely, in treating cancer using viruses, the present invention provides a composition comprising nc886 and thus allows the viruses to increase cancer therapeutic efficiency.

Solution to Problem

In the present invention, there may be provided a composition for enhancing virus production, comprising nc886 or an activator thereof.

In addition, in the present invention, there may be provided a method for producing viruses, comprising a step of adding nc886 or an activator thereof.

In addition, in the present invention, there may be provided a composition for enhancing activity of an oncolytic viral therapeutic agent, comprising nc886 or an activator thereof.

In addition, in the present invention, there may be provided a pharmaceutical composition for preventing or treating cancer, comprising: nc886 or an activator thereof; and an oncolytic viral therapeutic agent.

In addition, in the present invention, there may be provided a method for screening a candidate oncolytic viral therapeutic adjuvant for an oncolytic viral therapeutic agent, comprising steps of:
(a) contacting an nc886-expressing cell with a test substance and an oncolytic virus;
(b) analyzing an expression level of nc886 in the cell; and
(c) in a case where the test substance causes increased expression of nc886 as compared with a control that is not treated with the test substance, determining the test substance as a candidate oncolytic viral therapeutic adjuvant.

In addition, in the present invention, there may be provided a pharmaceutical composition for preventing or treating viruses, comprising an inhibitor for expression of nc886.

In addition, in the present invention, there may be provided a method for screening a candidate for treatment of a viral infection, comprising steps of:
(a) contacting an nc886-expressing cell with a test substance;
(b) analyzing an expression level of nc886 in the cell; and
(c) in a case where the test substance causes decreased expression of nc886, determining the test substance as a candidate for treatment of a viral infection.

Advantageous Effects of Invention

The present invention provides a pharmaceutical use of nc886 for providing a pro-viral environment. The composition comprising nc886 or an activator thereof, of the present invention, has effects capable of promoting virus replication to help virus production, and enhancing viral activity, in particular, efficacy of an oncolytic viral therapeutic agent. In addition, the composition comprising an nc886 antagonist, of the present invention, has prophylactic and therapeutic effects against viruses.

BRIEF DESCRIPTION OF DRAWINGS

FIGS. 1A-1G illustrate results showing that nc886 promotes virus replication. FIG. 1A illustrates a result obtained by performing Nothern blotting on indicated EtBr-stained ncRNAs including a loading control in indicated hepatocytes; FIGS. 1B and 1C illustrate results obtained by performing Western blotting on HCV and host human proteins, with or without knock-down of nc886, at indicated time points after infection with HCV; FIG. 1D illustrates a result obtained by measuring HCV virus mRNA at the indicated time points (transfection with anti-oligo for nc886 (designated as −886) or vtRNA1-1 (designated as −con) was performed 24 hours before infection with HCV, and "none" indicates transfection without anti-oligo); FIG. 1E illustrates results obtained by performing Western blotting with an anti-SeV antibody (SeV was used to infect the indicated cell lines. After the infection, the cells were collected at the indicated time points and lysed for Western blotting. Then, the bands were quantified); FIG. 1F illustrates results obtained by infecting 293 cells (with or without nc886 overexpression) with RSV at MOI of 1, and then preparing a total cell lysate and performing Western blotting for detecting viral proteins at various time points; and FIG. 1G illustrates a result obtained by infecting the indicated cell lines with AdV and measuring AdV particles.

FIGS. 2A-2E illustrate results showing that nc886 inhibits an IFN response. FIG. 2A illustrates a schematic diagram showing an IFN response that occurs upon infection with pathogens; FIG. 2B illustrates a result obtained by performing qRT-PCR measurement on IFNB1 upon treatment with Poly (I:C) (in which RNA was isolated at the indicated time points after transfection with Poly (I:C); IFNB1 and 18S rRNA were measured by qRT-PCR; the values were normalized to 18S rRNA; and the 0-hour value of 293T: vector was set to 1); FIG. 2C illustrates a result obtained by co-transfecting 293 cells (with or without 886 overexpression) with a luciferase reporter plasmid containing an IFN-β promoter element and an internal luciferase control plasmid (in which transfection with the luciferase plasmids was performed at 0 hour; transfection with SeV and RSV was performed at 9 hours; and the assay was completed at 24 hours); and FIGS. 2D and 2E illustrate results obtained by co-transfecting 293 cells (with or without 886 overexpression) with a luciferase reporter plasmid containing an internal luciferase control plasmid and a multimerizer at the IFN ISRE site, infecting the cells with MOCK or RSV/SeV at MOI of 1 15 hours after the transfection, and lysing the cells to measure luciferase activity (FIG. 2D) or collecting the supernatant to measure induction of RANTES (also IRF-3 regulatory mediator; FIG. 2E), 24 hours after the infection.

FIGS. 3A-3F illustrate results showing that nc886 induces an IFN response via various factors of the IFN promoter. FIG. 3A illustrates a result showing expression of IFNB1 mRNA; FIG. 3B illustrates a result showing that the NF-κB target mRNA is decreased by expression of nc886; FIG. 3C illustrates a result obtained by identifying activity of NF-κB using luciferase that shows activity of NF-κB; FIG. 3D illustrates a result showing that luciferase is identified using a reporter plasmid carrying four IRF3/IRF7-binding motifs; and FIGS. 3E and 3F illustrate results obtained by measuring activity of phospho-IRF3, which is an active form of IRF3, the results identifying that the activity decreases in a case where nc886 is expressed, and the activity increases in a case where nc886 is knocked down.

FIG. 4 illustrates a result showing that upon infection with adenovirus, expression of the viral gene increases in a case where PKR is knocked out; and under this genetic background, the expression decreases in a case where nc886 is also knocked out.

FIG. 5 illustrates a result showing that the cancer cell-killing activity (oncolytic effect) increases in the presence of nc886.

DETAILED DESCRIPTION OF INVENTION

Hereinafter, the present invention will be described in more detail.

nc886 of the present invention promotes virus replication. For example, in a case where cancer is treated using an oncolytic virus, nc886 has an effect of enhancing a therapeutic effect of the virus.

In the present invention, nc886 or an activator thereof may be used to enhance virus production. In particular, in a case of producing viruses, nc886 or an activator thereof may be added for stable virus production.

Hepatitis C virus replication takes place in some hepatocytes. The present inventors found that for Huh7-derived liver cell lines (Huh7, Huh7.5, FT3-7) in which Hepatitis C virus (HCV) is replicable, an expression level of nc886 was as high as in primary hepatocytes, whereas for the liver cell lines HepG2 and Hep3B in which HCV is not replicable, nc886 is silent (FIG. 1A). Therefore, to identify the role of nc886 in HCV replication, nc886 was knocked down using antisense oligonucleotide in Huh7.5 cell line. As a result, in the cells in which nc886 is knocked down, PKR was activated. It was observed that mRNA and protein levels of HCV also decreased. From this result, it was identified that nc886 is essential for HCV replication (FIGS. 1B and 1D). To identify that nc886 also exerted this effect on other types of viruses, additional experiments were performed using Sendai virus (SeV), respiratory cell virus (RSV), and adenovirus. 293T cells adapted to express nc886 were infected with RSV and SeV. As a result, it was identified that the proliferation of these viruses increased (FIGS. 1E to 1F). Furthermore, it was identified that the proliferation of adenovirus decreased significantly in Nthy-ori 3-1 cells in which nc886 was deleted by CRISPR-Cas technique (FIG. 1G).

HCV is a positive-sense RNA virus, SeV and RSV are negative-sense RNA viruses, and adenovirus is a double-stranded DNA virus. Thus, these viruses differ from one other in both viral gene expression and replication mechanism. It was observed that the proliferation of various viruses was all promoted by nc886, and thus nc886 is likely to promote the replication of a wide range of viruses. Based on these, it was hypothesized that inhibition of the host's innate immune response is a mechanism for the pro-viral role of nc886. To check this hypothesis, an effect of nc886 on interferon-β (IFN-β) signaling, which is important for primary host defense, was investigated. IFN-β contains three binding sites for three regulatory elements of AP-1, IRF, and NF-κB (FIG. 2A). Transfection with poly IC (synthetic ribonucleic acid that promotes interferon production) induced mRNA expression of IFN-β, whereas mRNA expression of IFN-β decreased in the presence of nc886 (FIG. 2B). The IFN-β promoter was activated by infection with poly IC, SeV, or RSV in 293T, which is a control cell line that does not express nc886, and the degree of activation decreased in 293T cells adapted to express nc886 (FIG. 2C). Transcriptional activation of ISGs in the IFN-β signaling pathway was mediated by the interferon-stimulated response element (ISRE). Luciferase expression was measured using ISRE. As a result, ISRE luciferase showed a similar result to IFN-β luciferase (FIG. 2D). From this result, it was identified that nc886 inhibited the IFN-3 signaling. In addition to IFN-β, the three regulatory elements of the IFN-β promoter, that is, AP-1, IRF, and NF-κB are required for production of chemokines such as RANTES; and it was identified that nc886 inhibited induction of RANTES upon infection with RSV (FIG. 2E).

For the three genes of NF-κB, AP-1, and IRF (FIG. 2A), which bind to the IFN-β promoter, their contribution was evaluated. Transfection with poly IC activated the IFN-β promoter, and this activation was remarkably decreased by nc886. In comparison, the IFN-β promoter was activated even in a case of transfection with the structurally activated phospho-mimetic IRF3 [=IRF3(5D)] mutant, and this activation was also decreased by nc886. From the viewpoint that IRF3 in an activated state was introduced, a result of decreased activation caused by nc886 under this condition should be interpreted as nc886 inhibiting NF-kB and AP-1, which proves that NF-kB and AP-1 make a contribution (FIG. 3A). As an experiment to support this, expression of NF-κB target mRNA was induced by poly IC; and it was observed that the NF-κB target mRNA was decreased by expression of nc886 (FIG. 3B). RSV was infected with 293T:vector (control cell line) and 293T:nc886 (cells expressing nc886) using luciferase that shows activity of NF-κB. As a result, it was identified that activity of NF-κB in 293T:nc886 (cells expressing nc886) decreased (FIG. 3C). To identify whether nc886 also inhibits the IRF3 element, luciferase was measured using a reporter plasmid carrying four IRF3/IRF7-binding motifs. The plasmid was activated by poly IC, and this activation was decreased by nc886 (FIG. 3D). The promoter was activated by IRF3 (5D). As a result, it was identified that the already activated mutant IRF3 (5D) was not affected by nc886, and thus the same induction occurs between 293T:vector and 293T:886. The activity of phospho-IRF3, which is an active form of IRF3, was measured. As a result, it was identified that the activity decreased in a case where nc886 is expressed, and the activity increased in a case where nc886 is knocked down (FIGS. 3E and 3F). Therefore, it was proven that the IRF pathway was also inhibited by nc886. In conclusion, it was proven that the three elements of NF-kB, AP-1, and IRF are all regulated by nc886, and these elements are known to be regulated by several pathways in addition to PKR.

In the present invention, the virus may include viruses belonging to the family Adenoviridae, Flaviviridae, Pneumoviridae, or Paramyxoviridae, and may preferably be adenovirus, Sendai virus, respiratory syncytial virus, or hepatitis C virus (HCV).

In the present invention, there may be provided a composition for enhancing activity of an oncolytic viral therapeutic agent, comprising nc886 or an activator thereof.

The role of PKR and nc886 in adenovirus proliferation was investigated. After infection with wild-type adenovirus, cells were collected 8 hours later. RNA was isolated therefrom. Then, among the RNAs transcribed from the adenovirus, E1B, an early gene, and VA I, an intermediate phase gene, were measured, and 18S rRNA expressed in the cells was measured together as a loading control. It was observed that the cells (lanes 1 to 2), in which PKR was deleted by the CRISPR-Cas method, showed increased expression of E1B and VA I as compared with the wild-type cells (lanes 5 to 6), which identifies that PKR is an antiviral protein. To check whether nc886 inhibits PKR and promotes adenovirus proliferation, an observation was made on a case where nc886 was deleted in a PKR-deleted state. If the above hypothesis is true, it was predicted that there would be no effect even in a case where nc886 is deleted because nc886 does not need to inhibit PKR in PKR-deleted cells. However, it was identified that in a case where even nc886 was deleted, the expression of E1B and VA I decreased clearly (FIG. 4). This result proves that nc886 is necessary for adenovirus proliferation, and shows that the mechanism of nc886 is separate from PKR inhibitory activity.

Adenovirus is one of oncolytic viruses that kill cells when released from the cells after proliferation therein. To identify the relationship between nc886 and adenovirus, which is an oncolytic virus, wild-type adenovirus was used to infect 293T.U6, which is a control cell line that does not express nc886, and 293T.U6:nc886, which is a cell line that expresses nc886. As a result, it was identified that the nc886-expressing cells showed lower cell viability (FIG. 5). From this result, it was identified that more oncolysis occurs in the presence of nc886. Thus, nc886 can be used to provide a composition for enhancing oncolytic virus activity.

In the present invention, the oncolytic virus may be adenovirus, reovirus, or Newcastle disease virus. The oncolytic virus proliferates well in cancer cells and destroys the cells. However, in some cancer cells, nc886 is silent; and according to the information obtained in the present invention, the oncolytic virus does not work well in these cancer cells due to decreased virus proliferation. In this case, it was identified that co-administration of the virus with nc886 could result in increased oncolytic efficiency.

In addition, in the present invention, there may be provided a pharmaceutical composition for preventing or treating cancer, comprising: nc886 or an activator thereof; and a viral therapeutic agent. In the present invention, the viral therapeutic agent may be an oncolytic virus, but is not limited thereto. It is clear that all these viruses and uses thereof fall within the scope of the present invention. The oncolytic virus may be adenovirus, reovirus, or Newcastle disease virus. The cancer may be breast cancer, skin cancer, bone cancer, prostate cancer, liver cancer, lung cancer, non-small cell lung cancer, brain cancer, laryngeal cancer, gallbladder cancer, pancreatic cancer, rectal cancer, parathyroid cancer, thyroid cancer, adrenal cancer, neural tissue cancer, head and neck cancer, colon cancer, gastric cancer, or bronchial cancer.

In the present invention, there may be provided a method for screening a candidate oncolytic viral therapeutic adjuvant for an oncolytic viral therapeutic agent, comprising steps of:
(a) contacting an nc886-expressing cell with a test substance and an oncolytic virus;
(b) analyzing an expression level of nc886 in the cell; and
(c) in a case where the test substance causes increased expression of nc886 as compared with a control that is not treated with the test substance, determining the test substance as a candidate oncolytic viral therapeutic adjuvant.

The oncolytic virus may be adenovirus, reovirus, or Newcastle disease virus.

In the present invention, there may be provided a pharmaceutical composition for preventing or treating viruses, comprising an inhibitor for expression of nc886. For example, the virus may be a virus belonging to the family Adenoviridae, Flaviviridae, Pneumoviridae, or Paramyxoviridae, and the virus may be Sendai virus, respiratory syncytial virus, or hepatitis C virus (HCV). nc886 promoted virus proliferation in both double-stranded DNA virus, positive-sense single-stranded RNA virus, and negative-sense single-stranded RNA virus. The inhibitor for expression of nc886 may be siRNA, shRNA, miRNA, ribozyme, DNAzyme, peptide nucleic acid (PNA), or antisense oligonucleotide. The inhibitor for expression of nc886 may include an antisense sequence for nc886 which consists of the nucleotide sequence of SEQ ID NO: 1. The nucleotide sequence of SEQ ID NO: 1 may be 5'-UCGAACCCCAGCACAGAGAU-3'. In the 5'-<u>UCGAACCCCAGCACAGAGAU</u>-3', each terminal 5 nts may include a nucleotide substituted with a 2'-O-methoxy group. That is, 5'-<u>UCGAA</u>CCCCAGCAC<u>AGAGA</u>U-3' may include a ribonucleotide, and 5'-UCGAA<u>CCCCAGCACA</u>GAGAU-3' may include a deoxy-ribonucleotide. There was phosphorothioate backbone modification between the nucleotides, In the present invention, there may be provided a method for screening a candidate for treatment of a viral infection, comprising steps of:
(a) contacting an nc886-expressing cell with a test substance;
(b) analyzing an expression level of nc886 in the cell; and
(c) in a case where the test substance causes decreased expression of nc886, determining the test substance as a candidate for treatment of a viral infection.

In the present invention, the virus may be a virus belonging to the family Flaviviridae, Pneumoviridae, or Paramyxoviridae, and the virus may be Sendai virus, respiratory syncytial virus, or hepatitis C virus (HCV).

Hereinafter, in order to help understand the present invention, the following examples are provided to describe the present invention in more detail. However, the following examples are merely provided to illustrate the present invention, and the scope of the present invention is not limited thereto. The examples of the present invention are provided to those of ordinary skill in the art so that the present invention is described in a more complete manner.

Example 1. Cell Lines, Viruses, and Antibodies

HEp-2 cells were purchased from ATCC and kept as described in X. Bao et al., Virology, 408, 224-231 (2010). Sendai virus was purchased from Charles River Laboratories, Inc. RST long strain was grown at 37° C. in HEp-2 cells, and purified with sucrose gradient as described in J. Ren et al., J. Gen. Virol., 92, 2153-2159 (2011). A cell line was produced from Nthy-ori-3-1 by deleting expression of PKR and nc886 using the CRISPR-cas technique (Oncotarget. 2016 Nov. 15; 7(46):75000-75012. doi: 10.18632/oncotarget.11852. LEE E K et al.), and kept in RPMI medium containing 10% FBS and 1% penicillin/streptomycin antibiotics. A viral titer was determined in HEp-2 cells by immunostaining, in which polyclonal biotin-conjugated goat anti-RSV antibody (Cat #: 7950-0104, Bio-rad) and streptavidin peroxidase polymer (Cat #: S2438, Sigma-Aldrich) were sequentially used as described above. A monoclonal antibody (Cat #A1978) against β-actin was purchased from Sigma. HEK-293T cells (American Type Culture Collection) were cultured at 5% $CO_2$ and 37° C. using DMEM medium containing 10% fetal bovine serum and 1% Antibiotic-Antimycotic. In the HEK-293T cells, U6 promoter was inserted into the pLPCX vector to construct the plasmid "pLPCX-U6", and the nc886 expression plasmid "pLPCX-U6-pre-886" was constructed therefrom. The 293T cells are a cell line in which expression of nc886 is silent. 293T.U6: nc886 is a cell line obtained by artificially expressing nc886 in the 293T cells, and 293T.U6 is a control cell line produced by using an empty vector at the time of producing 293T.U6: nc886 (RNA. 2011 June; 17(6):1076-89. doi: 10.1261/rna.2701111. Epub 2011 Apr. 25. PMID:21518807. Lee K. et al.). The adenovirus is type 5 wild-type virus and was provided by Dr. Alemany's laboratory (Spain). This virus was grown in HEK-293 cells, and then purified by the standard cesium chloride method (https://bio-protocol.org/bio101/e201). The virus titer was determined by a crystal violet staining method after infecting HEK-293 and HEK-293FT cells with the virus.

Example 2. Reporter Gene Assay

A plasmid containing the IFN-β promoter, and a plasmid containing multiple copies of the ISRE site of the IFN-β promoter linked to a luciferase reporter gene were transfected into the cells as described in Jeon S H et al., FEBS Lett., 21; 586(19):3477-84 2012 September. The logarithmically growing 293 cells were transfected 3-fold with a reporter plasmid using FuGene 6 (Roche, Indianapolis, IN) as described in Lee K et al. RNA, 17(6):1076-89, June 2011. 15 hours after transduction, the cells were treated with poly IC or infected with SeV or RSV for 2 hours or 15 hours, respectively. Luciferase was normalized to internal control Rr activity.

Example 3. HCV Experiment

Huh7.5 cells were grown in DMEM supplemented with 10% FBS, 1% MEM non-essential amino acid solution, 100 U/ml of penicillin, and 100 mg/ml of streptomycin (GIBCO). The Huh7.5 cells were seeded in a 6-well plate at $3 \times 10^5$/well and incubated overnight. The Huh7.5 cells were infected with HCV JFH1 (104 FFU/ml) supernatant, washed with PBS twice for 4 hours, and then the medium was exchanged with fresh medium to remove HCV JFH1. The cells were transfected with 100 nM anti-nc886 or anti-vtRNA using 15 ul RNAi-MAX. After 12, 24, and 48 hours of transfection, the cells were lysed with RIPA buffer (Thermofisher) containing a protease/phosphatase inhibitor (Thermofisher), and centrifuged at 13,000 rpm for 15 minutes to collect the protein-containing supernatant. The protein concentration in the cell extract was measured using BCA Protein Assay Kit (23225, Thermofisher). For each sample, 25 μg of total protein was electroporated on a 10% SDS-PAGE gel, and then transferred to a nitrocellulose membrane. The membrane was blocked with 5% skim milk for 1 hour, and primary antibodies of anti-HCV core (MA1-080, Thermo scientific), anti-NS3 (ab65407, Abcam), anti-NS5A from Charles Rice, anti-PKR (ab32052, Abcam), anti-phospho-PKR (ab32036), and beta-actin (A2228, Sigma) were blocked at 4° C. The same process as described above was performed except that another virus clone, Jc1 ($10^7$ FFU/ml), was used. 12, 24, 48, and 72 hours after transfection with anti-886 oligo, HCV RNA was isolated using QIAmp Viral RNA Mini Kit (52904, Qiagen) according to the manufacturer's instructions. A quantitative real-time PCR (qRT-PCR) experiment was performed using iQ5 Multicolor Real-time PCR Detection System (Bio-rad Laboratories). Forward primer: 5'-TGCACGGTCTACGAGAC-3' (SEQ ID NO: 2); probe: FAM-5'-CCGGGGCACTCGCAAGCACCC-3'-GMBH (SEQ ID NO: 3); and reverse primer: 5'-GACCCCCCCTCCCGG-GAG-3' (SEQ ID NO: 4) (target size: 222 bp).

Example 4. RANTES ELISA

The concentration of RANTES was determined by a commercial enzyme-linked immunosorbent assay (ELISA) according to the manufacturer's instructions (R&D Systems).

Example 5. PCR

To identify that nc886 promotes adenovirus proliferation, the expression of representative genes depending on cellular transcriptional phases was checked by RT-PCR. Infection with adenovirus was performed at multiplicity of infection (MOI)=5. After 8 hours, total RNA was extracted by the TRIzol (15596018, Invitrogen) method, and the amfiRivert cDNA Synthesis Platinum Master Mix (R5600, Gendepot) was used to prepare cDNA. The prepared cDNA was subjected to polymerase chain reaction, together with the viral genes E1B 55K and VAI RNA, and the human gene 18S rRNA used as a control, using amfiSure PCR Master Mix (2×) (P0311, Gendepot) with the primer nucleotide sequences disclosed in Table 1 below; and electrophoresis on agarose gel was performed for identification.

TABLE 1

| Primer nucleotide sequence | Primer name |
|---|---|
| CTGCGAGTGTGGCGGTAAACATAT (SEQ ID NO: 5) | E1B_55k_3377-400 |
| CTTCATCGCTAGAGCCAAACTCAG (SEQ ID NO: 6) | E1B_55k_3498-75 |
| GGGCACTCTTCCGTGGTC (SEQ ID NO: 7) | VAI_10620-37 |
| TTGTCTGACGTCGCACACCTG (SEQ ID NO: 8) | Ad_VAI_142-22 |
| CGGCTTTGGTGACTCTAGAT (SEQ ID NO: 9) | 18S rRNA 281-300 |
| GCGACTACCATCGAAAGTTG (SEQ ID NO: 10) | 18S rRNA 381-362 |

Example 6. Measurement of Cell Viability

The cell line indicated in the drawings was infected with adenovirus at multiplicity of infection (MOI)=5, and the cell viability was measured after 42 hours. The degree of viability was analyzed using CellTiter 96@ One Solution Cell Proliferation Assay (MTS) (G3581, Promega).

Example 7. Nc886 Promotes Virus Replication

Hepatitis C virus replication takes place in some hepatocytes. The present inventors found that for Huh7-derived liver cell lines (Huh7, Huh7.5, FT3-7) in which Hepatitis C virus (HCV) is replicable, an expression level of nc886 was as high as in primary hepatocytes, whereas for the liver cell lines HepG2 and Hep3B in which HCV is not replicable, nc886 is silent (FIG. 1A). Therefore, to identify the role of nc886 in HCV replication, nc886 was knocked down using antisense oligonucleotide in Huh7.5 cell line. As a result, in the cells in which nc886 is knocked down, PKR was activated. It was observed that mRNA and protein levels of HCV also decreased. From this result, it was identified that nc886 is essential for HCV replication (FIGS. 1B and 1D). To identify that nc886 also exerted this effect on other types of viruses, additional experiments were performed using Sendai virus (SeV), respiratory cell virus (RSV), and adenovirus. 293T cells adapted to express nc886 were infected with RSV and SeV. As a result, it was identified that the proliferation of these viruses increased (FIGS. 1E to 1F). Furthermore, it was identified that the proliferation of adenovirus decreased significantly in Nthy-ori 3-1 cells in which nc886 was deleted by the CRISPR-Cas technique (FIG. 1G).

Example 8. Nc886 Antagonizes Interferon Response

HCV is a positive-sense RNA virus, SeV and RSV are negative-sense RNA viruses, and adenovirus is a double-stranded DNA virus. Thus, these viruses differ from one other in both viral gene expression and replication mechanism. It was observed that the proliferation of various viruses was all promoted by nc886, and thus nc886 is likely to promote the replication of a wide range of viruses. Based on these, it was hypothesized that inhibition of the host's innate immune response is a mechanism for the pro-viral role of nc886. To check this hypothesis, an effect of nc886 on interferon-β (IFN-β) signaling, which is important for primary host defense, was investigated. IFN-β contains three binding sites for three regulatory elements of AP-1, IRF, and NF-κB (FIG. 2A). Transfection with poly IC (synthetic ribonucleic acid that promotes interferon production) induced mRNA expression of IFN-β, whereas mRNA expression of IFN-β decreased in the presence of nc886 (FIG. 2B). The IFN-β promoter was activated by infection with poly IC, SeV, or RSV in 293T, which is a control cell line that does not express nc886, and the degree of activation decreased in 293T cells adapted to express nc886 (FIG. 2C). Transcriptional activation of ISGs in the IFN-β signaling pathway was mediated by the interferon-stimulated response element (ISRE). Luciferase expression was measured using ISRE. As a result, ISRE luciferase showed a similar result to IFN-β luciferase (FIG. 2D). From this result, it was identified that nc886 inhibited the IFN-3 signaling. In addition to IFN-β, the three regulatory elements of the IFN-β promoter, that is, AP-1, IRF, and NF-κB are required for production of chemokines such as RANTES; and it was identified that nc886 inhibited induction of RANTES upon infection with RSV (FIG. 2E).

Example 9. Nc886 Inhibits IFN-β Promoter Through Inhibition of PKR

For the three genes of NF-κB, AP-1, and IRF (FIG. 2A), which bind to the IFN-β promoter, their contribution was evaluated. Transfection with poly IC activated the IFN-β promoter, and this activation was remarkably decreased by nc886. In comparison, the IFN-β promoter was activated even in a case of transfection with the structurally activated phospho-mimetic IRF3 [=IRF3(5D)] mutant, and this activation was also decreased by nc886. From the viewpoint that IRF3 in an activated state was introduced, a result of decreased activation caused by nc886 under this condition should be interpreted as nc886 inhibiting NF-kB and AP-1, which proves that NF-kB and AP-1 make a contribution (FIG. 3A). As an experiment to support this, expression of NF-κB target mRNA was induced by poly IC; and it was observed that the NF-κB target mRNA was decreased by expression of nc886 (FIG. 3B). RSV was infected with 293T:vector (control cell line) and 293T:nc886 (cells expressing nc886) using luciferase that shows activity of NF-κB. As a result, it was identified that activity of NF-κB in 293T:nc886 (cells expressing nc886) decreased (FIG. 3C). To identify whether nc886 also inhibits the IRF3 element, luciferase was measured using a reporter plasmid carrying four IRF3/IRF7-binding motifs. The plasmid was activated by poly IC, and this activation was decreased by nc886 (FIG. 3D). The promoter was activated by IRF3 (5D). As a result, it was identified that the already activated mutant IRF3 (5D) was not affected by nc886, and thus the same induction occurs between 293T:vector and 293T:886. The activity of phospho-IRF3, which is an active form of IRF3, was measured. As a result, it was identified that the activity decreased in a case where nc886 is expressed, and the activity increased in a case where nc886 is knocked down (FIGS. 3E and 3F). Therefore, it was proven that the IRF pathway was also inhibited by nc886. In conclusion, it was proven that the three elements of NF-kB, AP-1, and IRF are all regulated by nc886, and these elements are known to be regulated by several pathways in addition to PKR.

Example 10. Nc886 Promotes Adenovirus Proliferation

Adenovirus infects almost all cells that express the coxsackievirus and adenovirus receptor (CAR) on the cell surface, and is replicable therein. In general, it is known that adenovirus expresses viral genes after infection, whereas a host cell uses a defense system called PKR to control the virus proliferation. For Nthy-ori-3-1 cells in which PKR is deleted, after infection with the virus, the following result was obtained: RNA expression of the viral genes E1B 55K and VA I increased as compared with parental cells (from comparison of lanes 6 and 2 in FIG. 4). In the cells in which both nc886/PKR are knocked out, the expression of E1B and VAI decreased remarkably (from comparison of lanes 6 and 4 in FIG. 4). These results demonstrate that nc886 is required for AdV proliferation. In addition, from the viewpoint that PKR as well as nc886 is knocked out in this cell line, these results indicate that the reason why nc886 is necessary for AdV proliferation is not to inhibit PKR but to be intended for another mechanism.

Example 11. Nc886 Promotes Apoptosis by Adenovirus

293T.U6:nc886 grows slightly slower than 293T.U6 under a normal cell culture condition. After infection with adenovirus, it was identified that viability of nc886-expressing 293T decreased remarkably (FIG. 5). Since adenovirus is known to exhibit oncolysis when it comes out of the infected cell after proliferation, it can be concluded, along with the above RT-PCR results, that in nc886-expressing cells, the expression of adenovirus genes increases and thus promotes virus proliferation, thereby causing higher apoptosis.

The invention claimed is:

1. A method for promoting adenovirus proliferation, comprising:
a step of infecting nc886-expressing cell with adenovirus.

* * * * *

SEQUENCE LISTING

```
<160> NUMBER OF SEQ ID NOS: 10

<210> SEQ ID NO 1
<211> LENGTH: 20
<212> TYPE: RNA
<213> ORGANISM: Artificial
<220> FEATURE:
<223> OTHER INFORMATION: UCGAACCCCAGCACAGAGAU

<400> SEQUENCE: 1
ucgaacccca gcacagagau                                              20

<210> SEQ ID NO 2
<211> LENGTH: 17
<212> TYPE: DNA
<213> ORGANISM: Artificial
<220> FEATURE:
<223> OTHER INFORMATION: Forward primer

<400> SEQUENCE: 2
tgcacggtct acgagac                                                 17

<210> SEQ ID NO 3
<211> LENGTH: 21
```

```
<212> TYPE: DNA
<213> ORGANISM: Artificial
<220> FEATURE:
<223> OTHER INFORMATION: probe

<400> SEQUENCE: 3
ccggggcact cgcaagcacc c                                            21

<210> SEQ ID NO 4
<211> LENGTH: 18
<212> TYPE: DNA
<213> ORGANISM: Artificial
<220> FEATURE:
<223> OTHER INFORMATION: reverse primer

<400> SEQUENCE: 4
gaccccccct cccgggag                                                18

<210> SEQ ID NO 5
<211> LENGTH: 24
<212> TYPE: DNA
<213> ORGANISM: Artificial
<220> FEATURE:
<223> OTHER INFORMATION: Primer_E1B_55k_3377-400

<400> SEQUENCE: 5
ctgcgagtgt ggcggtaaac atat                                         24

<210> SEQ ID NO 6
<211> LENGTH: 24
<212> TYPE: DNA
<213> ORGANISM: Artificial
<220> FEATURE:
<223> OTHER INFORMATION: Primer_E1B_55k_3498-75

<400> SEQUENCE: 6
cttcatcgct agagccaaac tcag                                         24

<210> SEQ ID NO 7
<211> LENGTH: 18
<212> TYPE: DNA
<213> ORGANISM: Artificial
<220> FEATURE:
<223> OTHER INFORMATION: Primer_VAI_10620-37

<400> SEQUENCE: 7
gggcactctt ccgtggtc                                                18

<210> SEQ ID NO 8
<211> LENGTH: 21
<212> TYPE: DNA
<213> ORGANISM: Artificial
<220> FEATURE:
<223> OTHER INFORMATION: Primer_Ad_VAI_142-22

<400> SEQUENCE: 8
ttgtctgacg tcgcacacct g                                            21

<210> SEQ ID NO 9
<211> LENGTH: 20
<212> TYPE: DNA
<213> ORGANISM: Artificial
<220> FEATURE:
<223> OTHER INFORMATION: Primer_18S rRNA 281-300

<400> SEQUENCE: 9
```

```
cggctttggt gactctagat                                          20

<210> SEQ ID NO 10
<211> LENGTH: 20
<212> TYPE: DNA
<213> ORGANISM: Artificial
<220> FEATURE:
<223> OTHER INFORMATION: Primer_18S rRNA 381-362

<400> SEQUENCE: 10
gcgactacca tcgaaagttg                                          20
```